United States Patent
Benson et al.

(10) Patent No.: US 9,415,176 B1
(45) Date of Patent: Aug. 16, 2016

(54) AUTOINJECTOR HAVING AN END-OF-DOSE VISUAL INDICATOR

(71) Applicant: West Pharmaceutical Services, Inc., Exton, PA (US)

(72) Inventors: Paul Benson, Murchison, TX (US); Richard D. Gillespie, III, Athens, TX (US); Tommy G. Davis, Athens, TX (US)

(73) Assignee: West Pharmaceutical Services, Inc., Exton, PA (US)

( * ) Notice: Subject to any disclaimer, the term of this patent is extended or adjusted under 35 U.S.C. 154(b) by 0 days.

(21) Appl. No.: 14/602,961

(22) Filed: Jan. 22, 2015

(51) Int. Cl.
*A61M 5/50* (2006.01)
*A61M 5/20* (2006.01)
*A61M 5/32* (2006.01)

(52) U.S. Cl.
CPC .............. *A61M 5/5086* (2013.01); *A61M 5/20* (2013.01); *A61M 5/3202* (2013.01); *A61M 5/3213* (2013.01); *A61M 5/3216* (2013.01); *A61M 5/3243* (2013.01); *A61M 5/508* (2013.01)

(58) Field of Classification Search
CPC . A61M 5/5086; A61M 5/508; A61M 5/3202; A61M 5/3213; A61M 5/3216; A61M 5/322; A61M 25/00618; A61M 25/0631; A61M 5/50
USPC ................. 604/110, 111, 192, 194–198, 263; 128/919
See application file for complete search history.

(56) References Cited

U.S. PATENT DOCUMENTS

| 4,850,968 | A | * | 7/1989 | Romano | A61M 5/3243 604/110 |
| 5,176,643 | A | | 1/1993 | Kramer et al. | |
| 5,300,030 | A | | 4/1994 | Crossman et al. | |
| 5,338,310 | A | * | 8/1994 | Lewandowski | A61B 5/1438 604/110 |

(Continued)

FOREIGN PATENT DOCUMENTS

| EP | 2758102 B1 | 8/2015 |
| WO | 2011123024 A1 | 10/2011 |

(Continued)

OTHER PUBLICATIONS

Extended European Search Report issued Jun. 21, 2016 in EP Application No. 16152044.

*Primary Examiner* — Manuel Mendez
(74) *Attorney, Agent, or Firm* — Panitch Schwarze Belisario & Nadel LLP

(57) ABSTRACT

An autoinjector that automatically retracts a needle contained therein includes an injection assembly, having a plunger and a movable piston coupled to the plunger, a retraction assembly coupled to the injection assembly, and an end-of-dose visual indicator disposed within the retraction assembly. The retraction assembly includes an opaque section, a transparent or translucent section coupled to the opaque section, and a drug container having a hypodermic needle. The end-of-dose visual indicator is disposed within the retraction assembly such that the indicator moves upwardly from the opaque section of the retraction assembly to the transparent or translucent section of the retraction assembly upon full administration of a drug solution or medicine contained within the drug container. The end-of-dose visual indicator may be configured according to many preferred embodiments, among which may include a hollow cylinder, a split indicator ring, a co-extruded ring, and a multi-faceted polygonal cylinder.

13 Claims, 3 Drawing Sheets

(56) References Cited

U.S. PATENT DOCUMENTS

| | | | |
|---|---|---|---|
| 5,478,316 A | 12/1995 | Bitdinger et al. | |
| 5,599,309 A | 2/1997 | Marshall et al. | |
| 5,665,071 A | 9/1997 | Wyrick | |
| 6,099,504 A | 8/2000 | Gross et al. | |
| 6,159,181 A | 12/2000 | Crossman et al. | |
| 6,203,530 B1 | 3/2001 | Stewart, Sr. | |
| 6,221,053 B1 | 4/2001 | Walters et al. | |
| 6,367,802 B1 * | 4/2002 | Knapp | F16L 21/03 277/314 |
| 6,537,252 B1 | 3/2003 | Hansen | |
| 6,793,646 B1 | 9/2004 | Giambattista et al. | |
| 6,830,560 B1 | 12/2004 | Gross et al. | |
| 7,252,651 B2 | 8/2007 | Haider et al. | |
| 7,357,790 B2 | 4/2008 | Hommann et al. | |
| 7,442,185 B2 | 10/2008 | Amark et al. | |
| 7,449,012 B2 | 11/2008 | Young et al. | |
| 7,635,348 B2 | 12/2009 | Raven et al. | |
| 7,645,265 B2 | 1/2010 | Stamp | |
| 7,717,877 B2 | 5/2010 | Lavi et al. | |
| 7,736,333 B2 | 6/2010 | Gillespie, III | |
| 7,744,565 B2 | 6/2010 | Heiniger et al. | |
| 7,749,195 B2 | 7/2010 | Hommann | |
| 7,758,548 B2 | 7/2010 | Gillespie et al. | |
| 7,794,432 B2 | 9/2010 | Young et al. | |
| 7,806,866 B2 | 10/2010 | Hommann et al. | |
| 7,927,303 B2 | 4/2011 | Wyrick | |
| 7,955,304 B2 | 6/2011 | Guillermo | |
| 8,021,335 B2 | 9/2011 | Lesch, Jr. | |
| 8,043,262 B2 | 10/2011 | Streit et al. | |
| 8,048,035 B2 | 11/2011 | Mesa et al. | |
| 8,308,687 B2 | 11/2012 | Carrel et al. | |
| 8,308,695 B2 | 11/2012 | Laiosa | |
| 8,348,905 B2 | 1/2013 | Radmer et al. | |
| 8,357,120 B2 | 1/2013 | Moller et al. | |
| 8,376,998 B2 | 2/2013 | Daily et al. | |
| 8,491,530 B2 | 7/2013 | Maritan | |
| 8,496,619 B2 | 7/2013 | Kramer et al. | |
| 8,500,693 B2 | 8/2013 | Maritan | |
| 8,529,499 B2 | 9/2013 | Matusch | |
| 8,529,503 B2 | 9/2013 | Elmen et al. | |
| 8,529,510 B2 | 9/2013 | Giambattista et al. | |
| 8,529,518 B2 | 9/2013 | Larsen et al. | |
| 8,562,564 B2 | 10/2013 | Lesch, Jr. | |
| 8,591,463 B1 | 11/2013 | Cowe | |
| 8,591,465 B2 | 11/2013 | Hommann | |
| RE44,640 E | 12/2013 | Heiniger | |
| 8,641,668 B2 | 2/2014 | Matusch | |
| 8,647,299 B2 | 2/2014 | Stamp | |
| 8,647,306 B2 | 2/2014 | Schwirtz et al. | |
| 8,652,100 B1 | 2/2014 | Cowe | |
| 8,679,061 B2 | 3/2014 | Julian et al. | |
| 8,696,625 B2 | 4/2014 | Carrel et al. | |
| 8,696,628 B2 | 4/2014 | Grunhut | |
| 8,708,971 B2 | 4/2014 | Segal | |
| 8,728,027 B2 | 5/2014 | Jensen et al. | |
| 8,734,393 B2 | 5/2014 | Cleathero | |
| 8,747,357 B2 | 6/2014 | Stamp et al. | |
| 8,758,301 B2 | 6/2014 | Shang et al. | |
| 9,114,211 B2 | 8/2015 | Enggaard et al. | |
| 2001/0037087 A1 | 11/2001 | Knauer | |
| 2002/0095120 A1 | 7/2002 | Larsen et al. | |
| 2004/0236284 A1 | 11/2004 | Hoste et al. | |
| 2005/0222539 A1 | 10/2005 | Gonzales et al. | |
| 2006/0189938 A1 | 8/2006 | Hommann et al. | |
| 2007/0129686 A1 | 6/2007 | Daily et al. | |
| 2007/0173770 A1 | 7/2007 | Stamp | |
| 2007/0265568 A1 | 11/2007 | Tsals et al. | |
| 2009/0124981 A1 | 5/2009 | Evans | |
| 2009/0149809 A1 | 6/2009 | Bollenbach et al. | |
| 2009/0281496 A1 | 11/2009 | Matusch | |
| 2010/0016793 A1 | 1/2010 | Jennings et al. | |
| 2010/0016794 A1 | 1/2010 | Corrigan | |
| 2010/0100039 A1 | 4/2010 | Wyrick | |
| 2010/0160894 A1 | 6/2010 | Julian et al. | |
| 2011/0060279 A1 | 3/2011 | Altman et al. | |
| 2011/0178469 A1 | 7/2011 | Johnston et al. | |
| 2011/0226646 A1 | 9/2011 | Wyrick | |
| 2011/0319864 A1 | 12/2011 | Beller et al. | |
| 2012/0004608 A1 | 1/2012 | Lesch, Jr. | |
| 2012/0101475 A1 | 4/2012 | Wilmot et al. | |
| 2012/0289905 A1 | 11/2012 | Julian et al. | |
| 2012/0310172 A1 | 12/2012 | MacDonald et al. | |
| 2013/0041324 A1 | 2/2013 | Daniel | |
| 2013/0041347 A1 | 2/2013 | Daniel | |
| 2013/0053787 A1 | 2/2013 | Abry | |
| 2013/0060231 A1 | 3/2013 | Adlon et al. | |
| 2013/0060232 A1 | 3/2013 | Adlon et al. | |
| 2013/0079718 A1 | 3/2013 | Shang et al. | |
| 2013/0079725 A1 | 3/2013 | Shang | |
| 2013/0123710 A1 | 5/2013 | Ekman et al. | |
| 2013/0150800 A1 | 6/2013 | Kemp et al. | |
| 2013/0158508 A1 | 6/2013 | Cox et al. | |
| 2013/0190721 A1 | 7/2013 | Kemp et al. | |
| 2013/0190722 A1 | 7/2013 | Kemp et al. | |
| 2013/0204199 A1 | 8/2013 | Hourmand et al. | |
| 2013/0211330 A1 | 8/2013 | Pedersen et al. | |
| 2013/0218094 A1 | 8/2013 | Hommann et al. | |
| 2013/0237914 A1 | 9/2013 | Alexandersson | |
| 2013/0245553 A1 | 9/2013 | Mesa et al. | |
| 2013/0245562 A1 | 9/2013 | Kouyoumjian et al. | |
| 2013/0267898 A1 | 10/2013 | Hourmand et al. | |
| 2013/0281939 A1 | 10/2013 | Roberts et al. | |
| 2013/0289491 A1 | 10/2013 | Kramer et al. | |
| 2013/0310746 A1 | 11/2013 | Wozencroft | |
| 2013/0317431 A1 | 11/2013 | KraMer et al. | |
| 2013/0317434 A1 | 11/2013 | Fabien et al. | |
| 2013/0317435 A1 | 11/2013 | Fabien et al. | |
| 2013/0317480 A1 | 11/2013 | Reber et al. | |
| 2013/0324924 A1 | 12/2013 | Brereton et al. | |
| 2013/0331788 A1 | 12/2013 | KraMer et al. | |
| 2013/0338601 A1 | 12/2013 | Cowe | |
| 2014/0081239 A1 | 3/2014 | Cronenberg | |
| 2014/0088505 A1 | 3/2014 | Fabien et al. | |
| 2014/0114247 A1 | 4/2014 | Karlsson et al. | |
| 2014/0163477 A1 | 6/2014 | Quinn et al. | |

FOREIGN PATENT DOCUMENTS

| | | |
|---|---|---|
| WO | 2013057032 A1 | 4/2013 |
| WO | 2013077800 A1 | 5/2013 |
| WO | 2014060214 A1 | 4/2014 |

* cited by examiner

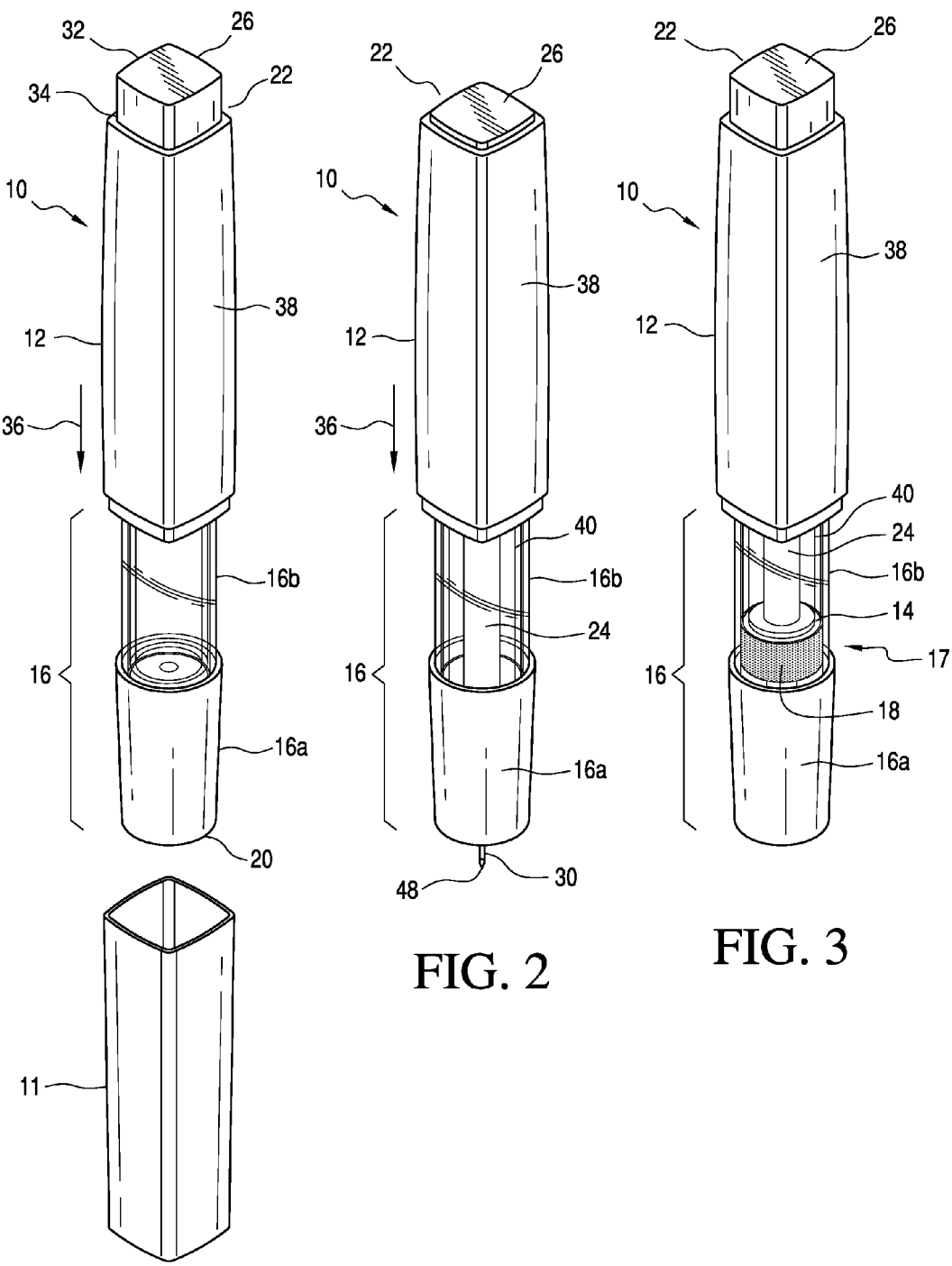

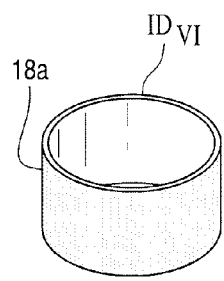
FIG. 4
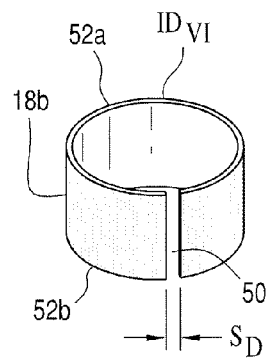
FIG. 5
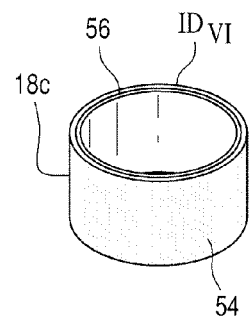
FIG. 6
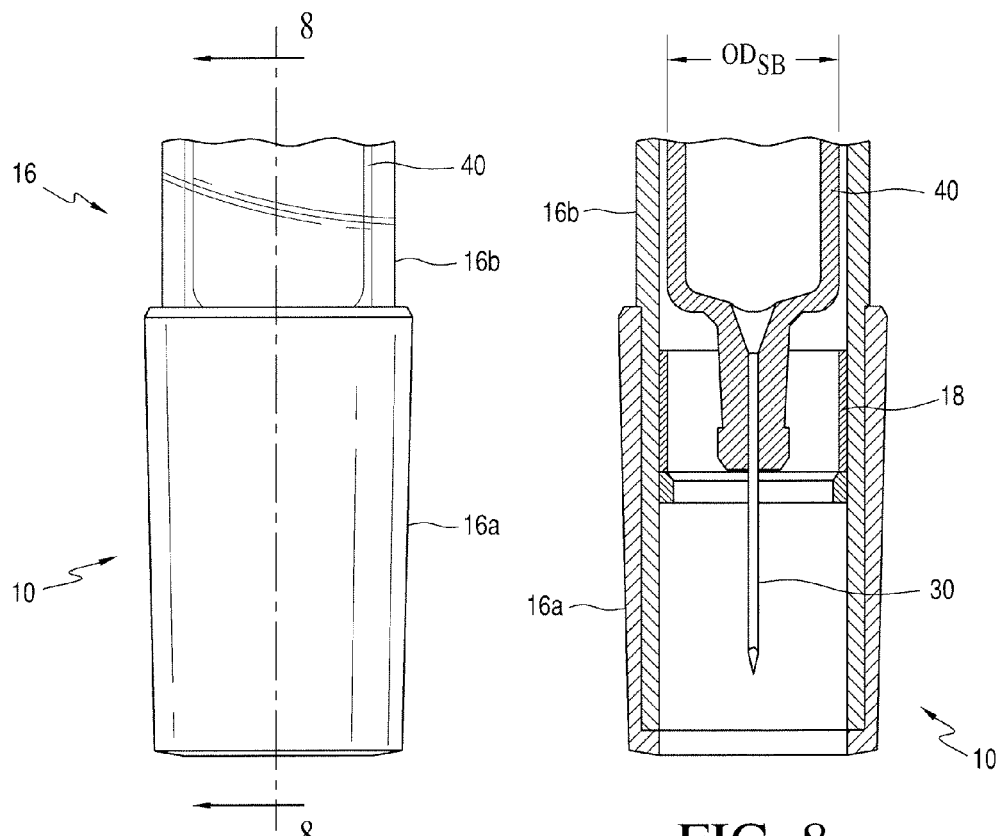
FIG. 7
FIG. 8

AUTOINJECTOR HAVING AN END-OF-DOSE VISUAL INDICATOR

BACKGROUND OF THE INVENTION

The field of the invention relates to automatic injection devices, i.e. autoinjectors, and particularly autoinjectors, including one or more end-of-dose visual indicators.

Automatic injection syringes, also referred to as "autoinjectors" include features that provide for an easy-to-use and automatic administration of an injectable drug solution or medicine. Autoinjectors are typically designed to have a push-pen design. The push-pen design allows an individual to initiate a self-injection literally at the push of a button or upon activation of a similar trigger that initiates self-injection. As such, autoinjectors are fairly simple to use, particularly in times when an individual may be experiencing stress, pain, and/or other medical ailments that would make self-injection with traditional syringes difficult.

Some types of autoinjectors are provided with the drug solution or medicine pre-loaded into a drug container, such as a syringe, or cartridge. When the drug solution or medicine is pre-loaded, the autoinjector is typically sold, having a predetermined, standardized unit dose. Without a distinct visual, audible and/or tactile indication to signal the complete dose has been administered, a user may become confused or impatient and remove the autoinjector from the injection site prematurely, losing some portion of the medicine. To address this issue, some autoinjectors described in the prior art, in particular non-retracting autoinjectors, come with instructions to the user to hold the injector against the injection site of the user much longer than the time actually required to complete the injection. To comply with these instructions, the user must therefore routinely experience the discomfort and distress of the hypodermic needle residing within the injection site longer than truly necessary.

For these reasons, among others, there is a need for improved autoinjectors that allow a user to clearly determine when the dose of medicine has been fully delivered. The embodiments of the invention fulfill this need and provide further related advantages, as described herein.

BRIEF SUMMARY OF THE INVENTION

In accordance with the preferred embodiments described herein, an autoinjector includes an injection assembly, having a plunger and a movable piston coupled to the plunger, a retraction assembly coupled to the injection assembly, and an injectable drug container having a proximal end and a distal end, with the distal end being configured to receive an end-of-dose visual indicator. Preferably, the retraction assembly includes an opaque section and a transparent or translucent section coupled to the opaque section. The end-of-dose visual indicator is disposed within the retraction assembly and configured to cooperate with the distal end of the drug container and move in concert with the drug container from within the opaque section of the retraction assembly into the transparent or translucent section of the retraction assembly upon completion of both administration of a drug solution or medicine contained within the drug container and retraction of the drug container. The end-of-dose visual indicator may be configured in a number of embodiments; among the preferred embodiments are a hollow cylinder, a split hollow cylinder, a co-extruded ring having at least two different material constituents, and a multi-faceted polygonal cylinder.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 is a front perspective view of an autoinjector, in accordance with preferred embodiments of the present invention, before injection;

FIG. 2 is a front perspective view of the autoinjector shown in FIG. 1 during injection;

FIG. 3 is a front perspective view of the autoinjector shown in FIG. 1 after injection and after full administration of a drug solution or medicine;

FIG. 4 is a front perspective view of a first embodiment of an end-of-dose visual indicator;

FIG. 5 is a front perspective view of a second embodiment of an end-of-dose visual indicator;

FIG. 6 is a front perspective view of a third embodiment of an end-of-dose visual indicator;

FIG. 7 is a slightly enlarged partial front elevational view of the autoinjector shown in FIG. 1;

FIG. 8 is a cross-sectional view of the autoinjector shown in FIG. 7, taken along line 8-8 of FIG. 7;

DETAILED DESCRIPTION OF THE INVENTION

Figure 9:
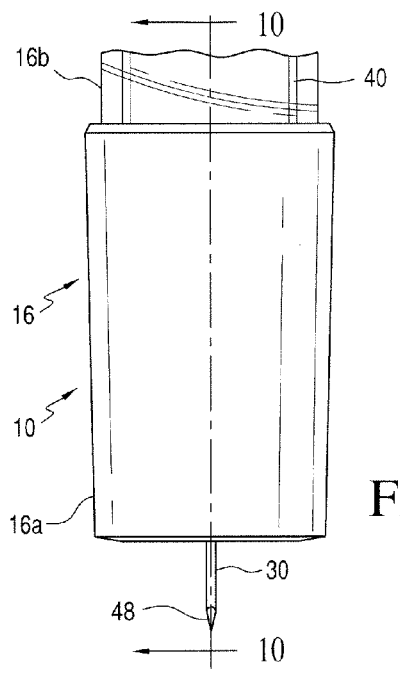
FIG. 9 is a slightly enlarged partial front elevational view of the autoinjector shown in FIG. 2.

Reference will now be made in detail to the present embodiments of the invention illustrated in the accompanying drawings. Wherever possible, the same or like reference numbers will be used throughout the drawings to refer to the same or like features. It should be noted that the drawings are in simplified form and are not drawn to precise scale.

In reference to the disclosure herein, for purposes of convenience and clarity only, directional terms used in conjunction with the following description of the drawings should not be construed to limit the scope of the invention in any manner not explicitly set forth. Unless specifically set forth herein, the terms "a", "an", and "the" are not limited to one element but instead should be read as meaning "at least one." The terminology includes the words noted above, derivatives thereof and words of similar import. It should also be noted that the terms "first", "second", "third", "upper", "lower", and the like may be used herein to modify various elements. These modifiers do not imply a spatial, sequential, or hierarchical order to the modified elements unless specifically stated.

Referring to the Figs. and in particular to FIGS. 1-3 and 8, there is shown an autoinjector 10 preferably of the type capable of both automatic injection of a drug solution or medicine 2 via a drug container 40 with an affixed needle 30 and automatic retraction of the drug container/needle 40, 30 after completion of the injection. Other preferred autoinjector embodiments are contemplated such as the embodiments described by illustrative example in U.S. Pat. No. 8,123,724, wherein a drug cartridge with a separate needle, rather than a syringe with an affixed needle is described. The autoinjector 10 includes, among other elements, a cap 11, an injection assembly 12, a retraction assembly 16, a drug container assembly 17 comprising a drug container 40, hypodermic needle 30 and movable piston 14. The drug container assembly 17 provides containment for the medicine or drug solution 2. The autoinjector 10 also defines an injection or distal end 20 for placement against the injection site of a user and an actuation or proximal end 22 for actuating the injection assembly 12 using, in some preferred embodiments, an actuation button 26. For purposes of explanation, the autoinjector 10 is shown not including all features typically included in autoinjectors containing a drug solution or medicine 2 (e.g. cartridges and springs).

During use, the autoinjector 10 goes through at least three stages: (1) a pre-injection stage (FIG. 1); (2) an injection stage (FIG. 2); and (3) a post-injection, needle retraction stage (FIG. 3). During the first, pre-injection stage (FIG. 1), the cap 11 is first removed from the injection end 20. Referring to FIGS. 1, 7 and 8; the actuation button 26 has not been pushed and the end-of-dose visual indicator 18 and the needle 30 are contained within an opaque section 16a of the retraction assembly 16. In FIG. 8, a partial view of the drug container 40, including the drug solution or medicine 2 is shown.

Figure 10:
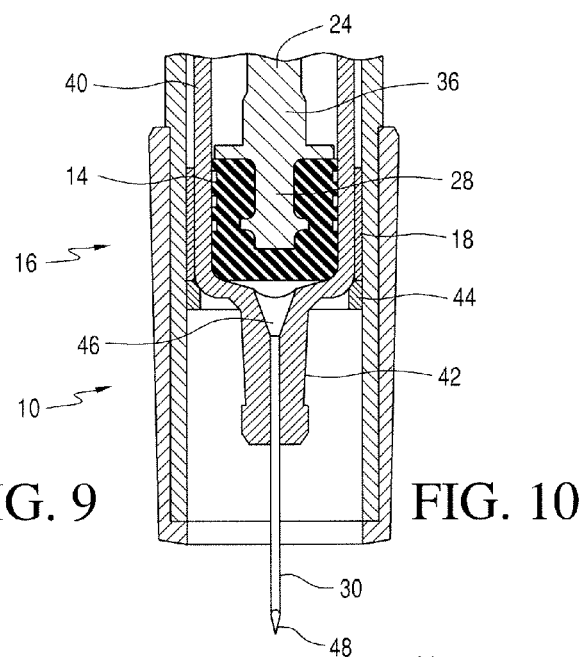
FIG. 10 is a cross-sectional view of the autoinjector shown in FIG. 9, taken along line 10-10 of FIG. 9.

During the second, injection stage, as shown in FIGS. 2, 9, and 10, the cap 11 has been removed, the injection end 20 is in engagement with the skin of a user (not shown), the actuation button 26 has been pushed, and the drug container 40 moves distally to engage the end-of-dose visual indicator 22. In embodiments where the needle 30 is permanently affixed to the drug container 40, as the drug container 40 moves forward, a portion of the needle 30 extends out of the distal end 20 of the opaque section 16a of the retraction assembly 16 and into the injection site (not shown), i.e. tissue, of the recipient of the injection. Once the drug container 40 extends forward to a fully distal position whereupon the needle 30 protrudes outward from the retraction assembly 16 to the fullest extent allowable by the physical constraints of the autoinjector 10, the medicine or drug solution 2 is forced out of the drug container 40 through the needle 30 and into the injection site of a user. During the injection stage, the end-of-dose visual indicator 18 remains hidden by the opaque section 16b of the retraction mechanism 16 (as shown particularly in FIG. 10); however, engagement between the end-of-dose visual indicator 18 and the drug container 40 has been established.

Figure 11:
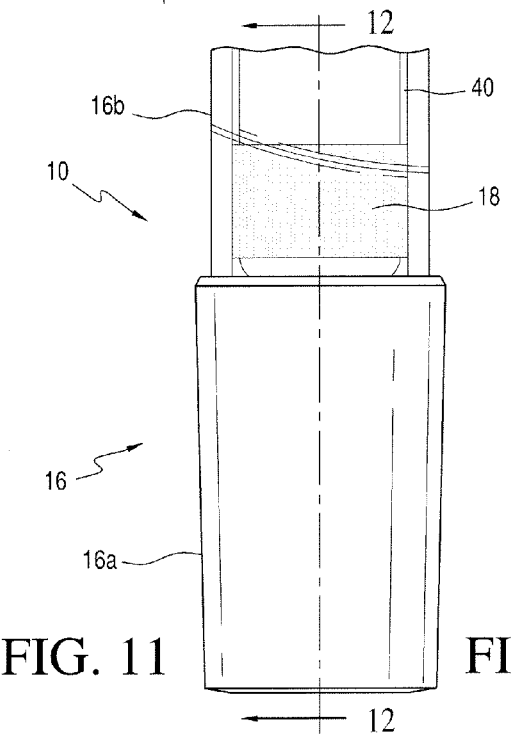
FIG. 11 is a slightly enlarged partial front elevational view of the autoinjector shown in FIG. 3.
Figure 12:
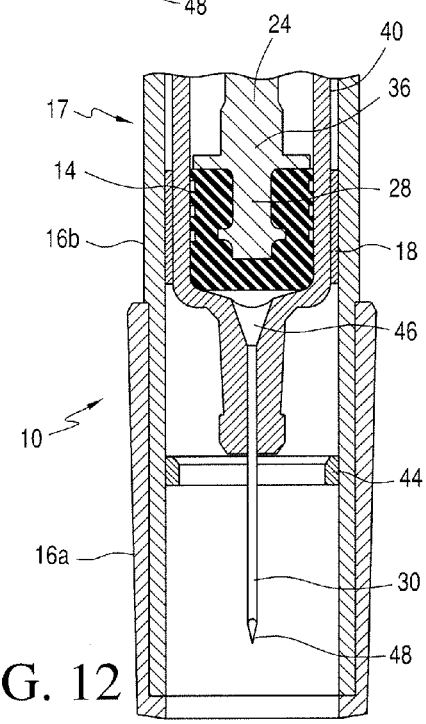
FIG. 12 is a cross-sectional view of the autoinjector shown in FIG. 11, taken along line 12-12 of FIG. 11.

FIGS. 3, 11, and 12 show the autoinjector 10 during the third, post-injection and retraction stage. In this final stage, the end-of-dose visual indicator 18, now physically engaged with drug container 40, has moved proximally in concert with the drug container 40 to a fully-retracted position. Once retracted, the end-of-dose visual indicator 18 becomes visible in the transparent or translucent section 16b of the retraction assembly 16. Concurrently, the needle 30 being permanently affixed to the drug container 40, retreats from an extended position external to the opaque section 16a of the retraction assembly 16 to a retracted position internal to the opaque section 16a. During the third stage, the end-of-dose visual indicator 22 (FIG. 3) is visually displayed in the transparent or translucent section 16a of the autoinjector 10, informing a user that the injection is complete, the needle 30 is retracted and the full dose of the drug solution or medicine 2 is administered.

The injection assembly 12 includes various elements configured to act on the retraction assembly 16. For the sake of brevity, these elements, their cooperative interrelation, and the general utility described in preferred embodiments of an autoinjector mechanisms contemplated to be relevant to the invention defined herein are described in among others U.S. Pat. Nos. 6,387,078, 7,674,246, 7,988,675, 8,048,029, and 8,123,724. The disclosures of each of the aforementioned patents are hereby incorporated by reference herein.

Injection assemblies of the types described in the aforementioned patents typically include an injection spring (not shown), a movable piston 14, a plunger 24 coupled to the movable piston 14, and an actuation button 26 configured to act upon the plunger 24, among other elements. In some injection assemblies, a portion of the elements of the injection assembly 12 is contained, during the pre-injection stage, within an upper housing 38. The plunger 24 may also include an integrated coupler 28 that connects the plunger 24 and the movable piston 14. The actuation button 26 may be further defined at the activation end 22 and include an upper end 32 and a lower end 34. In some injection assemblies, the upper end 32 may protrude outwardly from the injection assembly 12, while the lower end 34 may extend distally inwardly into the injection assembly 14. The lower end 34 is also coupled to the plunger 24 to release energy stored in the injection spring and propel the plunger 24 in an injection direction 36. A driving end 36 (FIGS. 9 and 11) of the plunger 24 may also be configured to act on the retraction assembly 16. For example, as the plunger 24 and the moveable piston 14 move toward the injection direction 36, under the influence of the injection spring, the retraction assembly 16 may become energized.

In the injection assembly disclosed herein, the retraction assembly 16 includes an opaque section 16a, a transparent or translucent viewing section 16b having a portion disposed within the opaque section 16a, a needle 30, a transparent or translucent drug container 40 having a needle hub 42 that holds the needle 30, a retraction spring (not shown) and a buttress 44. The buttress may, alternatively, be incorporated as a counterbore shoulder in the innermost bore of the retraction assembly 16 in the axial location of the proximally-disposed surface of the buttress 44. The function of buttress 44 is to provide axial support to the distal end of the end-of-dose visual indicator 18. The needle 30 is preferably a hypodermic needle that includes an entrance section 46 and a tissue penetrating exit tip 48. Transparent or translucent elements of the retraction assembly 16 such as the transparent or translucent section 16b and the transparent or translucent drug container 40 allow a user to visually assess the progress of dose administration and view the end-of-dose visual indicator 18 when the dose has been fully administered. The transparent or translucent elements 16b, 40 may also allow medical providers to verify correct dose volume, verify that the drug solution has not degraded, and confirm the full dose was administered.

The injection and retraction assemblies 12, 16 disclosed herein are preferably secured to one another in a snap fit manner. As such, each assembly may include corresponding tabs and slots or other structure that provide a snap fit connection.

FIGS. 4 through 6 show exemplary embodiments of an end-of-dose visual indicator 18. Preferably, the end-of-dose visual indicator 18 is manufactured from one or more materials that provide a bright, and noticeable color, e.g. orange or green, which contrasts with the overall color scheme of the autoinjector 10. The end-of-dose visual indicator 18 may also include finishes and/or graphics or other indicia that increase visibility of the indicator 18 through transparent or translucent elements 16a, 40 and provide aesthetic value.

In a first embodiment, shown in FIG. 4, an end-of-dose visual indicator 18 is configured as a hollow cylinder 18a. The hollow cylinder 18a preferably has an inner diameter, $ID_{VT}$, which is at least slightly less than the outer diameter, $OD_{SB}$, of the drug container 40. The fit between the inner diameter, $ID_{VT}$, of the hollow cylinder 18a and the outer diameter, $OD_{SB}$, of the drug container 40 is such that the cylinder 18a is prevented from moving into the transparent or translucent section 16b of the retraction assembly 16 during normal handling of the autoinjector 10 (i.e. before activation of the injection assembly), as shown in FIG. 7. The fit between the inner diameter, $ID_{VT}$, of the hollow cylinder 18a and the outer diameter, $OD_{SB}$, of the drug container 40 is also not so tight as to prevent the drug container 40 from entering into the inner diameter, $ID_{VT}$, of the hollow cylinder 18a when the drug container 40 is acted upon by the injection assembly 12 during the injection stage, as shown particularly in FIG. 9.

In a second embodiment, shown in FIG. 5, an end-of-dose visual indicator 18 is configured as a split cylindrical indicator ring 18b, including a slot or slit 50 that fully extends in an axial direction between outer edges 52a, 52b of the ring 18b. Here, the ring 18b has an $ID_{VT}$ that is also smaller than the outer diameter, $OD_{SB}$, of the drug container 40. The range of the $ID_{VT}$ provides for greater variation in tolerance ranges, thereby reducing the possibility that the indicator ring 18b would enter the transparent or translucent section 16a prematurely, fail to achieve sufficient interference for the indicator ring 18b to secure onto the drug container 40, and/or prevent forward movement of the drug container 40, during the injection stage. The slot distance SD is sized to allow the indicator ring 18b to spread open and accommodate the outer diameter, $OD_{SB}$, of the drug container 40, during the injection stage, as shown particularly in FIG. 9. Hoop stress of the indicator ring 18b caused by dimensional interference, during the injection stage, exerts pressure on the outer diameter, $OD_{SB}$, of the drug container 40 to ensure that the drug container will not slide out of the indicator ring 18b during the retraction stage, as shown in FIG. 11.

In a third embodiment, shown in FIG. 6, an end-of-dose visual indicator 18 is configured as a co-extruded ring 18c. The co-extruded ring 18c includes an outer polymer section 54 and an inner polymer section 56. The outer polymer section 54 has material properties that provide an axial stiffness and flexural modulus that prevent buckling failure and increase hoop stress of the co-extruded ring 18c. The inner polymer section 56 has material properties that provide for tackiness and adhesion.

In a fourth embodiment (not shown), an end-of-dose visual indicator 18 is configured as a multi-faceted polygonal cylinder 18d. The multi-faceted polygonal cylinder 18d includes a plurality of segments 19 with each segment 19, being defined by an arc length A and a segment width W. The multi-faceted polygonal cylinder 18d has an innermost dimension $D_{VT}$ radially measured across the facets of the polygon, which is at least slightly less than the outer diameter, $OD_{SB}$, of the drug container 40. In addition, the total arc length, $T_A$ of the segments is approximately equal to the exterior circumference $C_{DC}$ of the drug container 40. When drug container 40 inserted into the end-of-dose visual indicator, the drug container 40 will exert a force onto the multi-faceted polygonal cylinder 18d that causes contact between the container 40 and the cylinder 18d. The force will cause the cylinder 18d to deform and become more circular, resulting in a radially inward-disposed retention force at approximately the midpoint of each segment 19.

The autoinjector 10, as shown in FIGS. 1-2 and other variations of autoinjectors may include any of the end-of-dose visual indicator configurations 18a, 18b, 18c, 18d described herein.

While the present disclosure has been described with reference to one or more exemplary embodiments of autoinjectors and end-of-dose visual indicators, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the appended claims.

We claim:

1. An auto-injector, comprising:
   an injection assembly, including a plunger and a movable piston coupled to the plunger;
   a retraction assembly coupled to the injection assembly, the retraction assembly comprising an opaque section and a transparent or translucent section coupled to the opaque section;
   an injectable drug container having a proximal end and a distal end, the distal end being configured to receive an end-of-dose visual indicator; and
   an end-of-dose visual indicator disposed within the retraction assembly and configured to cooperate with the distal end of the drug container and move in concert with the drug container from within the opaque section of the retraction assembly into the transparent or translucent section of the retraction assembly upon completion of administration of the drug solution or medicine contained within the drug container and retraction of the drug container.

2. The autoinjector according to claim 1, wherein the autoinjector operates in a pre-injection stage, an injection stage, and a post-injection, needle retraction stage.

3. The auto-injector according to claim 2, wherein the end-of-dose visual indicator is a hollow cylinder, having an inner diameter that fits against an outer diameter of the drug container, and the fit between the inner diameter of the hollow cylinder and the outer diameter of the drug container substantially prevents the hollow cylinder from moving into the transparent or translucent section of the retraction assembly during the pre-injection stage drug container.

4. The auto-injector according to claim 2, wherein the end-of-dose visual indicator is a hollow cylinder, having an inner diameter that fits against an outer diameter of the drug container, and the fit between the inner diameter of the hollow cylinder and the outer diameter of the drug container allows the outer diameter of the drug container to enter into the inner diameter of the hollow cylinder during the injection stage.

5. The autoinjector according to claim 2, wherein the end-of-dose visual indicator is a co-extruded ring.

6. The autoinjector according to claim 5, the co-extruded ring comprises an outer polymer section and an inner polymer section.

7. The autoinjector according to claim 1, wherein the end-of-dose visual indicator is as a split indicator ring, having a slot that fully extends between outer edges of the split indicator ring.

8. The autoinjector according to claim 7, wherein the slot defines a slot distance sized to allow the indicator ring to spread open and accommodate the outer diameter of the drug container.

9. The autoinjector according to claim 1, wherein the retraction assembly is directly coupled to the injection assembly.

10. The autoinjector according to claim 1, wherein the end-of-dose visual indicator is within the transparent or translucent section of the retraction assembly until after completion of administration of the drug solution or medicine.

11. The autoinjector according to claim 1, wherein the end-of-dose visual indicator is separate from the drug container prior to administration of the drug solution or medicine and is coupled to the drug container upon completion of administration of the drug solution or medicine.

12. An auto-injector, comprising:
an injection assembly, including a plunger and a movable piston coupled to the plunger;
a retraction assembly coupled to the injection assembly, the retraction assembly comprising an opaque section and a transparent or translucent section coupled to the opaque section;
an injectable drug container having a proximal end and a distal end, the distal end being configured to receive an end-of-dose visual indicator; and
an end-of-dose visual indicator disposed within the retraction assembly and configured to cooperate with the distal end of the drug container and move in concert with the drug container from within the opaque section of the retraction assembly into the transparent or translucent section of the retraction assembly upon completion of administration of the drug solution or medicine contained within the drug container and retraction of the drug container;
wherein the autoinjector operates in a pre-injection stage, an injection stage, and a post-infection, needle retraction stage; and
wherein the end-of-dose visual indicator is a co-extruded ring comprising an outer polymer section and an inner polymer section, the outer polymer section having an axial stiffness and flexural modulus that prevent buckling failure and increase hoop stress of the co-extruded ring as the autoinjector goes from the injection stage to the post-injection, needle retraction stage.

13. An auto-injector, comprising:
an injection assembly, including a plunger and a movable piston coupled to the plunger,
a retraction assembly coupled to the injection assembly, the retraction assembly comprising an opaque section and a transparent or translucent section coupled to the opaque section;
an injectable drug container having a proximal end and a distal end, the distal end being configured to receive an end-of-dose visual indicator; and
an end-of-dose visual indicator disposed within the retraction assembly and configured to cooperate with the distal end of the drug container and move in concert with the drug container from within the opaque section of the retraction assembly into the transparent or translucent section of the retraction assembly upon completion of administration of the drug solution or medicine contained within the drug container and retraction of the drug container;
wherein the autoinjector operates in a pre-injection stage, an injection stage, and a post-injection, needle retraction stage;
wherein the end-of-dose visual indicator is a co-extruded ring comprising an outer polymer section and an inner polymer section; and
wherein the inner polymer section provides for tackiness and adhesion as the autoinjector goes from the injection stage to the post-injection, needle retraction stage.

* * * * *